(12) United States Patent
Wang et al.

(10) Patent No.: US 10,092,901 B2
(45) Date of Patent: Oct. 9, 2018

(54) MICROPLATE

(71) Applicant: Yantai AusBio Laboratories Co., Ltd., Yantai, Shandong (CN)

(72) Inventors: Zhaoqiang Wang, Yantai (CN); Wolfgang Mann, Neudrossenfeld (DE)

(73) Assignee: Yantai AusBio Laboratories Co., Ltd., Yantai (CN)

( * ) Notice: Subject to any disclaimer, the term of this patent is extended or adjusted under 35 U.S.C. 154(b) by 182 days.

(21) Appl. No.: 15/302,185

(22) PCT Filed: Mar. 24, 2015

(86) PCT No.: PCT/CN2015/074991
§ 371 (c)(1),
(2) Date: Oct. 6, 2016

(87) PCT Pub. No.: WO2015/154622
PCT Pub. Date: Oct. 15, 2015

(65) Prior Publication Data
US 2017/0043337 A1 Feb. 16, 2017

(30) Foreign Application Priority Data
Apr. 7, 2014 (EP) .................... 14163772

(51) Int. Cl.
*B01L 3/00* (2006.01)
*B01L 9/00* (2006.01)
*G01N 21/07* (2006.01)
*G01N 33/80* (2006.01)
(Continued)

(52) U.S. Cl.
CPC ............ *B01L 3/5025* (2013.01); *B01L 3/508* (2013.01); *B01L 3/5085* (2013.01);
(Continued)

(58) Field of Classification Search
CPC ..... B01L 2300/0829; B01L 2300/0636; B01L 3/5085; B01L 2200/12; B01L 2300/0851;
(Continued)

(56) References Cited

U.S. PATENT DOCUMENTS 8,076,126 B2 12/2011 Jakubowicz et al.
2004/0187958 A1* 9/2004 Viola .................. B01L 3/06
141/329

(Continued)

FOREIGN PATENT DOCUMENTS

CA 2458827 A1 8/2004
CN 101629952 A 1/2010
(Continued)

OTHER PUBLICATIONS

PCT/CN2015/074991, International Search Report, dated Jun. 19, 2015, pp. 1-5.
(Continued)

*Primary Examiner* — Jennifer Wecker
(74) *Attorney, Agent, or Firm* — The Harris Firm

(57) ABSTRACT

A Microplate comprising a plurality of wells (2) is arranged in a two-dimensional array, wherein each well (2) is inclined or pivotably mounted in the microplate (1) so that the wells (2) align with the direction of a centrifugal force during centrifuging of the microplate (1).

27 Claims, 19 Drawing Sheets

(51) Int. Cl.
*G01N 35/02* (2006.01)
*G01N 35/04* (2006.01)

(52) U.S. Cl.
CPC .......... *B01L 3/50855* (2013.01); *B01L 9/523* (2013.01); *G01N 21/07* (2013.01); *G01N 33/80* (2013.01); *G01N 35/028* (2013.01); *G01N 35/04* (2013.01); *B01J 2219/00315* (2013.01); *B01J 2219/00317* (2013.01); *B01L 2200/028* (2013.01); *B01L 2200/12* (2013.01); *B01L 2300/0636* (2013.01); *B01L 2300/0819* (2013.01); *B01L 2300/0829* (2013.01); *B01L 2300/0851* (2013.01); *B01L 2300/0858* (2013.01); *B01L 2300/123* (2013.01); *B01L 2400/0409* (2013.01); *G01N 2035/0449* (2013.01)

(58) Field of Classification Search
CPC ................. B01L 3/50855; B01L 9/523; B01L 2200/028; B01L 2300/0819; B01L 3/508; B01L 3/5025; B01L 2300/0858; B01L 2300/123; B01L 2400/0409; B01J 2219/00317; B01J 2219/00315; G01N 21/07; G01N 33/80; G01N 35/028; G01N 35/04; G01N 2035/0449
See application file for complete search history.

(56) References Cited

U.S. PATENT DOCUMENTS

| | | |
|---|---|---|
| 2005/0161400 A1 | 7/2005 | Pitt et al. |
| 2008/0220481 A1* | 9/2008 | Mortillaro .......... B01L 3/50855 |
| | | 435/91.2 |
| 2010/0015726 A1 | 1/2010 | Jakubowicz et al. |
| 2011/0152128 A1 | 6/2011 | Herrmann |
| 2012/0288887 A1 | 11/2012 | Haga |

FOREIGN PATENT DOCUMENTS

| | | |
|---|---|---|
| CN | 203259531 U | 10/2013 |
| EP | 2 636 452 A1 | 9/2013 |
| EP | 13179437.2 | 2/2015 |
| WO | WO2013/117606 | 8/2013 |

OTHER PUBLICATIONS

PCT/CN2015/074991, Written Opinion of the International Search Report, dated Jun. 19, 2015, pp. 1-4.
EP 14163772.8, European Search Report, dated Feb. 16, 2015, pp. 1-17.

* cited by examiner

MICROPLATE

CROSS REFERENCE TO PRIOR APPLICATION(S)

This application is a U.S. National Stage Patent Application of PCT International Patent Application Ser. No. PCT/CN2015/074991 (filed on Mar. 24, 2015) under 35 U.S.C. § 371, which claims priority to European Patent Application Ser. No. EP14163772.8 (filed on Apr. 7, 2014), which are all hereby incorporated by reference herein in their entireties.

TECHNICAL FIELD

The present invention relates to a microplate for centrifuging a plurality of samples.

BACKGROUND

From WO 2013/117606 it is known to centrifuge microplates. A centrifuge for centrifuging microplates has a large diameter so that all wells of the microplate are uniformly centrifuged. Different materials contained in a well form after centrifuging layers. A more compact centrifuge causes problems in that such layers are tilted in the reaction wells which are placed in the outer region of the microplate. These tilted layers can often not be correctly detected with an automatic optical inspection device.

US 2008/220481 A1 discloses a microplate which can be put together like a kit comprising a tray assembly and a plurality of sample plates designed to fit into the tray assembly. The tray assembly comprises a frame and is capable of accommodating the sample plates side by side in the plate receiving portion. Each of the sample plates contains a plurality of individual sample wells arranged in a grid. The authors of US 2008/220481 A1 address the problem that the different processes during laboratory work get more complicated and that the amount of automation increases. The disclosed microplate which can be put apart, allowing the processing of several different sample patches.

The construction is rigid and does not allow that the wells align with the direction of a centrifugal force during centrifuging of the microplate.

US 2011/0152128 A1 discloses an enhanced microplate and retention device for selectively retaining tube inserts within the microplate and a dynamic microplate having a selectable number of interchangeable microwells. FIGS. 4A-4G show microwell plates with removable sample well strips, which, once put into the microwell, form a rigid construction.

EP 2 636 452 A1 refers to a process for the production of a reaction chamber assembly. FIGS. 2-4 disclose strips of sample wells which can be fit into a frame for a microplate. The figures demonstrate that the wells are put within the microplate frame in a way that they are not moveable to align with the direction of a centrifugal force during centrifugation.

On one hand there is a need for simultaneously centrifuging a large amount of samples which can be achieved by centrifuging a microplate on the other hand there is a need to embody a centrifuge as compact as possible as such devices should be integrated into roboter systems comprising a plurality of different devices.

SUMMARY

An object of the present invention is to provide a microplate for centrifuging a plurality of samples which allows a reliable testing of the centrifuged samples, even if the radius for centrifuging is small.

A further object of the present invention is to provide a microplate which allows to carry out a method for determining the result of an agglutination reaction with a high reliability and a high throughput.

The objects of the present invention are solved by a microplate as defined in the independent claims. Advantageous embodiments of the present invention are defined in the corresponding subclaims.

A microplate according to the present invention comprises a plurality of wells arranged in a two-dimensional array, wherein each well is inclinable or pivotably mounted in the microplate so that the wells align with the direction of the centrifugal force during centrifuging of the microplate.

As the wells of the microplate align with the direction of a centrifugal force during centrifuging of the microplate, the centrifugal force is acting in a direction corresponding to an axis of the corresponding well. Different materials in the wells form layers which extend perpendicular to this axis. This secures that the content of the wells can be reliably automatically optically tested, even if the radius for centrifuging is small.

If the reaction wells are not inclinable or pivotably mounted in the microplate, then the centrifugal force is tilted with respect to the axis of some reaction wells. This is particularly the case for reaction wells having an axis which is offset from a rotational axis of the centrifuging rotation. In such wells the layers of the different materials are tilted with respect to the axis of the reaction wells which could cause false results.

Preferably the reaction wells are elastically inclinable or pivotably arranged in the microplate, so that the reaction wells return to their initial position after centrifuging of the microplate.

According to a preferred embodiment the microplate comprises a frame and several longitudinal struts each comprising a row of wells, wherein the struts are pivotably arranged in the frame.

Such a strut can comprise at its ends a mounting pin, wherein the mounting pins are arranged in an upper section of the struts and form a mounting element for a pivotable mounting of the struts in the frame.

The frame can comprise recesses for mounting the mounting pins of the struts.

According to a further embodiment of the microplate, the microplate comprises a frame and an insert, wherein the insert comprises the plurality of reaction wells which form a two-dimensional array and the frame has at least one support section, which has a concave curvature for supporting the insert during centrifuging of the microplate. Preferably, the frame comprises two curved support sections each provided for supporting an edge section of the insert, wherein the two curved support sections are arranged diametrically opposite.

The insert comprises reaction wells being arranged in rows and columns. Preferably the insert comprises stiffening means in the direction of the rows and not in the direction of the columns or vice versa. Thus the insert is flexible in one direction but not in the other direction. Such stiffening elements can be e.g. intermediate wall sections which extend between neighboring reaction wells.

Preferably, the microplate, particularly a frame and/or an insert of a microplate, are made of an elastically deformable material.

According to a method of the present invention for centrifuging a plurality of samples, the samples are contained in wells of a microplate, particularly a microplate having a two-dimensional array of reaction wells, wherein during centrifuging the wells align to the direction of the centrifugal force.

In this method a microplate according to the above-described embodiments can be used.

The microplate is preferably rotated around a horizontal axis. When the microplate is rotated around a horizontal axis, then the openings of the reaction wells have not to be sealed. This allows an easy integration of a centrifuging step in an automatic system.

A method for determining the result of an agglutination reaction comprises the following steps:
  a reaction step of allowing a sample to react with a reagent in a well, wherein a microplate is used having a plurality of wells arranged in a two-dimensional array, wherein each well is inclinable or pivotable mounted in the microplate so that the wells align with the direction of a centrifugal force during centrifuging of the microplate
  a centrifugation step of rotating the microplate so that a bottom wall of the well will be arranged outwards with respect to a rotational axis,
  an imaging step of taking at least one image of the top side of the microplate and at least one image of the bottom side of the microplate,
  a determination step of determining the sample in said well to be positive or negative with respect to an agglutination reaction, wherein the color intensity and/or the gray level of said well in the images of the top side and the bottom side of the microplate are compared.

With this method a difference in the color intensity and/or the gray level of a certain well at the top side and the bottom side of the well is determined. Such a difference can be detected with high accuracy. Disturbing conditions, such as background light, have usually the same impact on both pictures of the top side and the bottom side of a well so that they are eliminated by comparing the color intensities and/or the gray levels of the top side and the bottom side of the corresponding reaction well. This makes the method very robust and reliable. This method is suitable for an industrial application for testing thousands or millions of samples automatically without any human intervention.

Furthermore, the provision of a two-dimensional array allows simultaneously to carry out a plurality of agglutination reactions and determination of a plurality of agglutination reactions. Due to detecting wells from the bottom side as well as from the top side, it is not necessary to use only a one-dimensional arrangement of reaction wells as it is known from e.g. U.S. Pat. No. 8,076,126 B2.

Preferably, the microplate is rotated around a horizontal axis in the centrifugation step. This facilitates the integration of the centrifugation step in an automatic system. Sample carried centrifuges having a horizontal rotational axis are described in WO 2013/117606 A1 and EP 13179437.2. The EP 13179437.2 is not yet published. The documents WO 2013/117606 A1 and EP 13179437.2 are incorporated by reference.

According to a preferred embodiment, an incubation step can be carried out before the centrifugation step for accelerating the agglutination reaction.

The reaction products, namely agglutinated probe sample parts, can be separated from the reaction educts, namely non-agglutinated probe sample parts, in the centrifugation step by means of a separation material, such as a gel material or a bead matrix. The bead matrix functions as a filter material, which retains the agglutinated sample parts, particularly clamped blood cells, on the top of the bead matrix, wherein the non-agglutinated sample parts penetrate the bead matrix and are collected at the bottom portion of the corresponding well. Using a gel matrix, the non-agglutinated sample parts are separated by the agglutinated sample parts in that the non agglutinated sample parts which penetrate the gel matrix during the centrifugation step to the bottom of the reaction well, wherein the larger agglutinated sample parts are retained on the top side of the gel matrix or in the gel matrix.

The reagent can be provided on the top of the separation material or the separation material can be mixed within the suspension containing a reagent. The reagent can comprise antibodies and/or antigens which react with a predetermined sample. If the gel matrix is mixed with the reagent, the agglutination reaction takes place in the gel matrix and the agglutinated products are kept in the gel matrix, where the reaction takes place.

In case a substrate is needed in order to make an antigen/antibody reaction visible, this can be included in the gel as well. It can also be located at the bottom and the top location only.

A microplate for determining products of agglutination reactions comprises a plurality of wells arranged in a two-dimensional array, wherein at least one of said wells comprises a separation section which contains a separation material such as a gel or a bead matrix, wherein the separation section comprises at least one conical portion which is tapered downwards, so that sample material penetrating the separation material will be concentrated.

The concentration of a sample material which penetrates the separation material enhances the color intensity or gray level in the picture of the bottom side of the well, because this sample material is concentrated in the center of the reaction well. This facilitates the automatic optical analysis. it also improves the reliability of the test, because it makes it easier to compare the color intensities or grey levels of the top and bottom side of the reaction well.

The reaction wells preferably comprise a filling section at the top end of the wells, wherein the cross-sectional area of the filling section is larger than a cross-section area of the separation section.

The microplate preferably comprises at least 96 wells. Such a microplate can comprise at least 300 and particularly 384 or at least 1000 or particularly 1536 wells.

The inner height of the reaction wells is preferably in the range of 5 mm to 25 mm, and particularly 10 mm to 20 mm or 10 mm to 15 mm.

According to a further aspect of the invention, a testing apparatus comprises a centrifuge and a camera for detecting the top side of a reaction well and a further camera for detecting the bottom side of the reaction well. This testing apparatus comprises a control unit for carrying out a method as described above.

Preferably, the testing apparatus comprises a loading mechanism for horizontally loading a microplate into the centrifuge and for horizontally discharging the microplate from the centrifuge. Line cameras can be provided along the loading path of the microplates for detecting the top surface and the bottom surface of the microplate. The line cameras extend transversally to the moving direction of the microplates.

The testing apparatus preferably comprises pipetting means for automatically filling the reaction wells with a separation material such as gel material. This allows to use only the reaction wells of a microplate which are needed.

Other reaction wells can be left empty. Thus, using a microplate having a plurality of reaction wells achieves a high throughput with low costs because only reaction wells are loaded with separation material and reagents which are actually used.

BRIEF DESCRIPTION OF DRAWINGS

The present invention will be explained in greater detail below in conjunction with the accompanying drawings. In the drawings:

FIG. 1b is a partially cut perspective view of the frame according to FIG. 1a, FIG. 1c is a partially cut perspective view of one of the struts according to FIG. 1a, FIG. 1d is a longitudinal sectional view of one of the struts according to FIG. 1a, FIG. 1e is a partially cut perspective view of the microplate according to FIG. 1a;

| List of references | | | |
|---|---|---|---|
| 1 | microplate | 2 | reaction well |
| 3 | opening | 4 | bottom wall |
| 5 | filing section | 6 | transfer section |
| 7 | separation section | 8 | upper part |
| 9 | lower part (conical portion) | 10 | collection section |
| 13 | testing apparatus | 14 | centrifuge |
| 15 | front platform | 16 | centrifuge section |
| 17 | driving section | 18 | rim |
| 19 | rotor | 20 | shaft |

-continued

| List of references | | | |
|---|---|---|---|
| 21 | plate tray | 22 | base wall |
| 23 | U-rail | 24 | rotation axis |
| 25 | stopper | 26 | microplate carrier |
| 27 | coupling element | 28 | front side wall |
| 29 | opening | 30 | loading mechanism |
| 31 | flexible elongated beam | 32 | inner wall |
| 33 | free end | 34 | upper strand |
| 35 | lower strand | 37 | stepper motor |
| 38 | magnetic element | 39 | flange |
| 40 | counterweight | 41 | leg |
| 42 | rim | 43 | pipetting nozzel |
| 44 | upper line camera | 45 | lower line camera |
| 50 | frame | 51 | strut |
| 52 | mounting pin | 53 | tapered lower edge |
| 54 | longitudinal sidewall | 55 | lateral sidewall |
| 56 | recess | 57 | V-shaped bottom wall |
| 58 | sidewall | 59 | platelet |
| 60 | slit | 61 | axis |
| 62 | intermediate wall section | 63 | frame |
| 64 | insert | 65 | strip |
| 66 | collar | 67 | longitudinal sidewall |
| 68 | lateral sidewall | 69 | upper edge |
| 70 | upper edge | 71 | frame |
| 72 | longitudinal sidewall | 73 | groove |
| 74 | bottom wall | 75 | rear wall |
| 76 | bow | 77 | lower edge |

DETAILED DESCRIPTION OF EMBODIMENTS

FIGS. 1a-1e show a first embodiment of a microplate 1 according to the invention. The microplate comprises 384 reaction wells 2 being arranged in a two-dimensional array of 16×24 wells.

The microplate 1 is made of a transparent, inert plastic material such as polycarbonate.

Figure 1A:
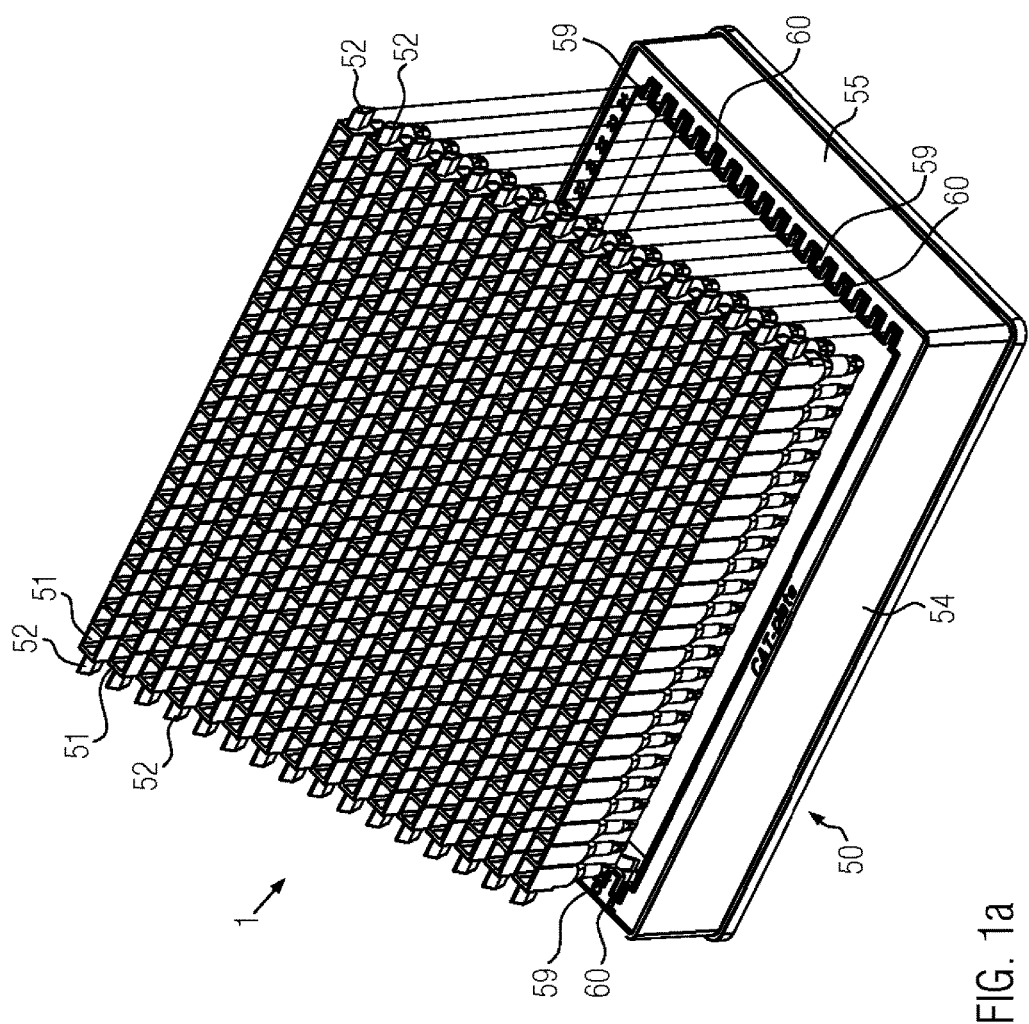
FIG. 1a shows a first embodiment of a microplate comprising a frame and a plurality of struts in a perspective explosion view.
Figure 1B:
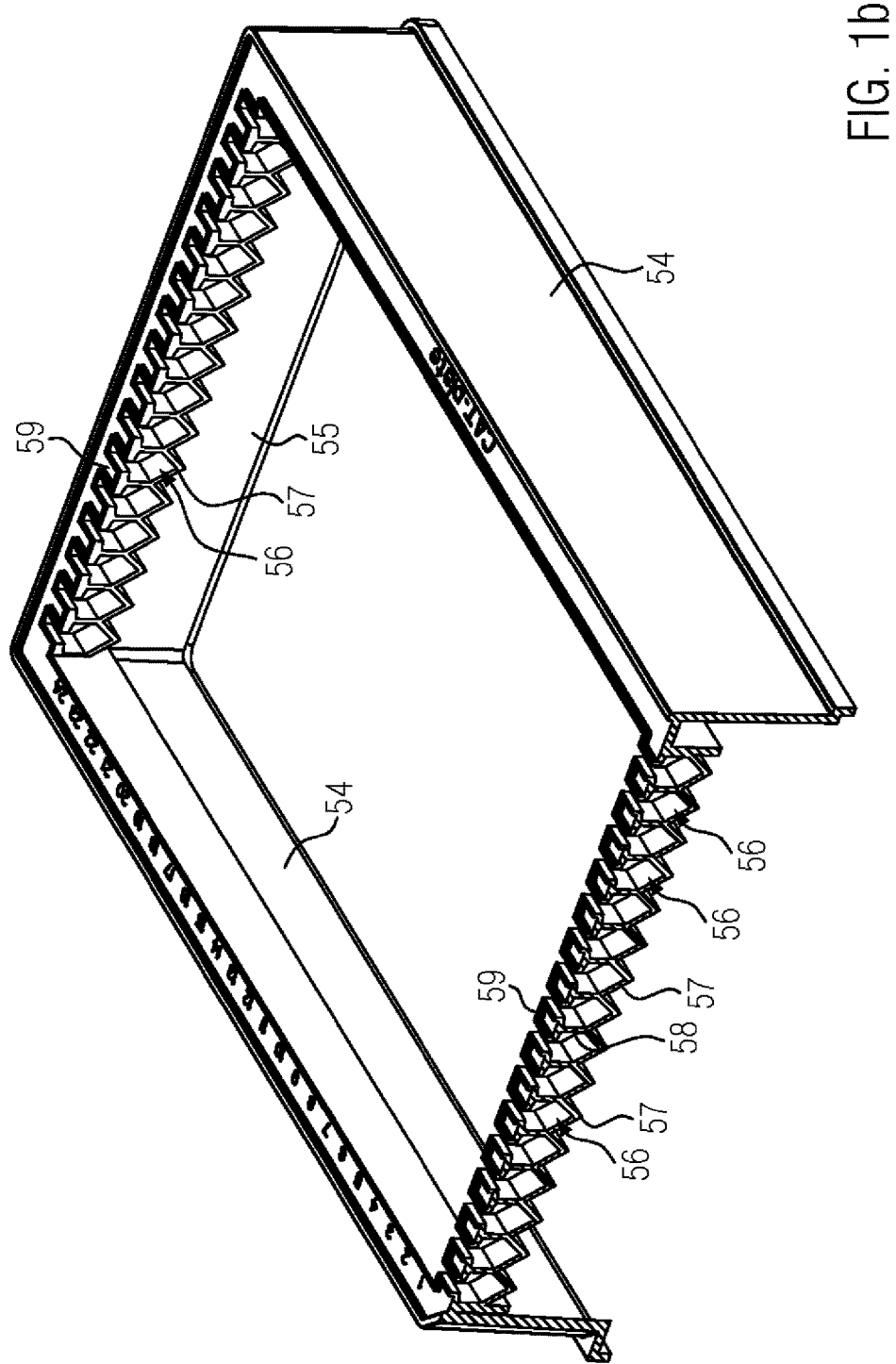
Figure 1C:
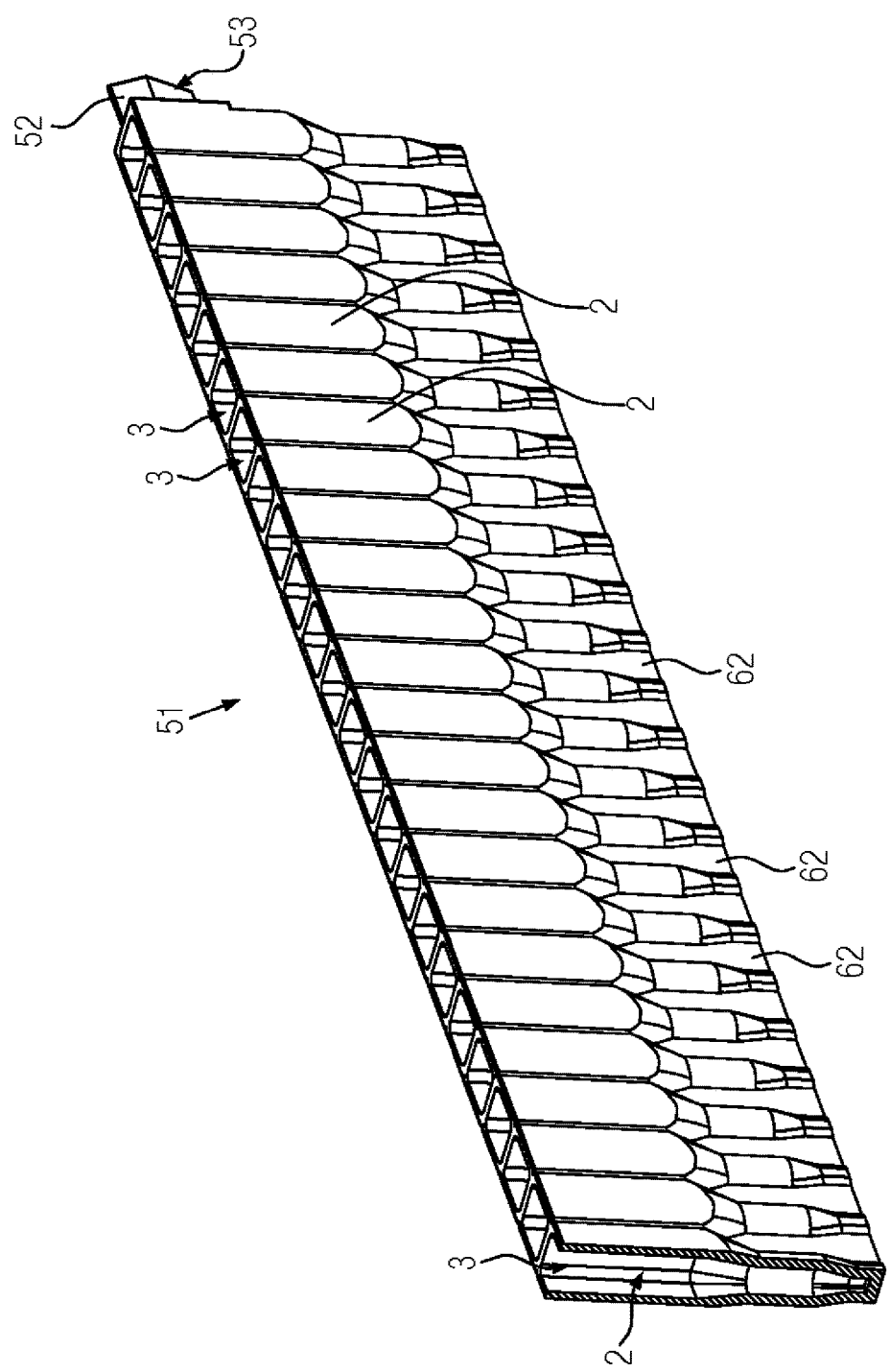
Figure 1D:
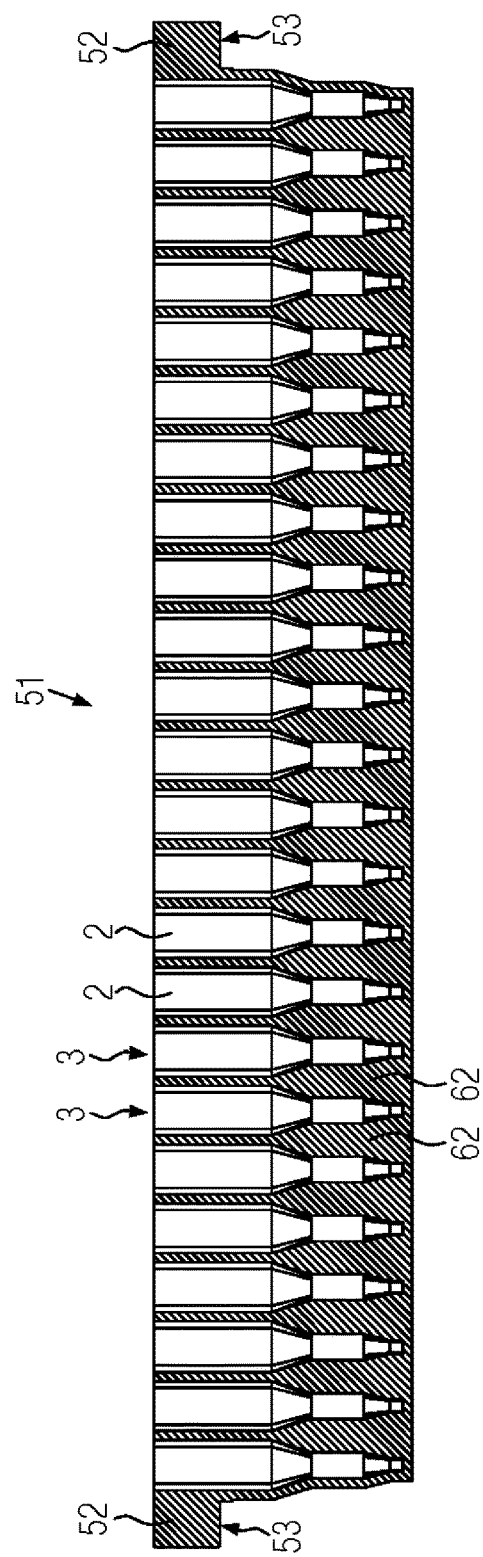

This first embodiment of the microplate 1 comprises a frame 50 and several longitudinal struts 51. Each strut 51 (FIG. 1c, 1d) is a longitudinal body made of an inert plastic material and defining a plurality of said reaction wells 2. The reaction wells 2 are arranged in a row in each strut 51. The reaction wells are arranged parallel to each other. The reaction wells 2 have openings 3 which are directed to the top. Each strut 51 comprises at is opposite ends a mounting pin 52. The mounting pins 52 are arranged in an upper section of the struts. The cross-sectional form of the mounting pins 52 is a rhombus, so that the mounting pins 52 have a tapered lower edge 53 (FIG. 1c, 1d).

The frame 50 comprises two longitudinal sidewalls 54 and two lateral sidewalls 55. Recesses 56 for retaining the mounting pins 52 are provided on the inner side of the lateral side walls 55. The recesses 56 are provided at the upper sections of the lateral sidewalls 55. Each recess 56 is defined by a V-shaped bottom wall 57 and two vertical sidewalls 58. The recesses 56 are arranged adjacent to each other so that each sidewall 58 defines on one side, one of said recesses 56 and on the other side another recess 56. A platelet 59 is provided on each top end of the sidewalls 58. The platelets 59 form a crenellated cover of the recesses 56, wherein between each pair of neighboring platelets 59 a slid 60 is defined which is a little bit smaller than the width of the mounting pins 52. The frame 50 and thus the platelets 59 are formed from an elastic plastic material, so that the mounting pins may be snapped through the slit 60.

The recesses 56 are open to the inner section of the frame 50. Pairs of recesses 56 are provided directly opposite to each other at the opposite lateral sidewalls 55, wherein, wherein the distance of such a pair of recesses 56 corresponds to the distance of the opposite mounting pins 52 of a strut 51.

The tapered lower edge 53 of the mounting pins 52 is sharper than the V-shaped bottom wall 57 of the recesses 56, so that the tapered lower edges 53 of the struts 51 abut pivotable on the V-shaped bottom wall 57.

In the present embodiment the frame 50 can take-up 16 struts 51, wherein each strut 51 comprises 24 reaction wells 2.

Figure 1E:
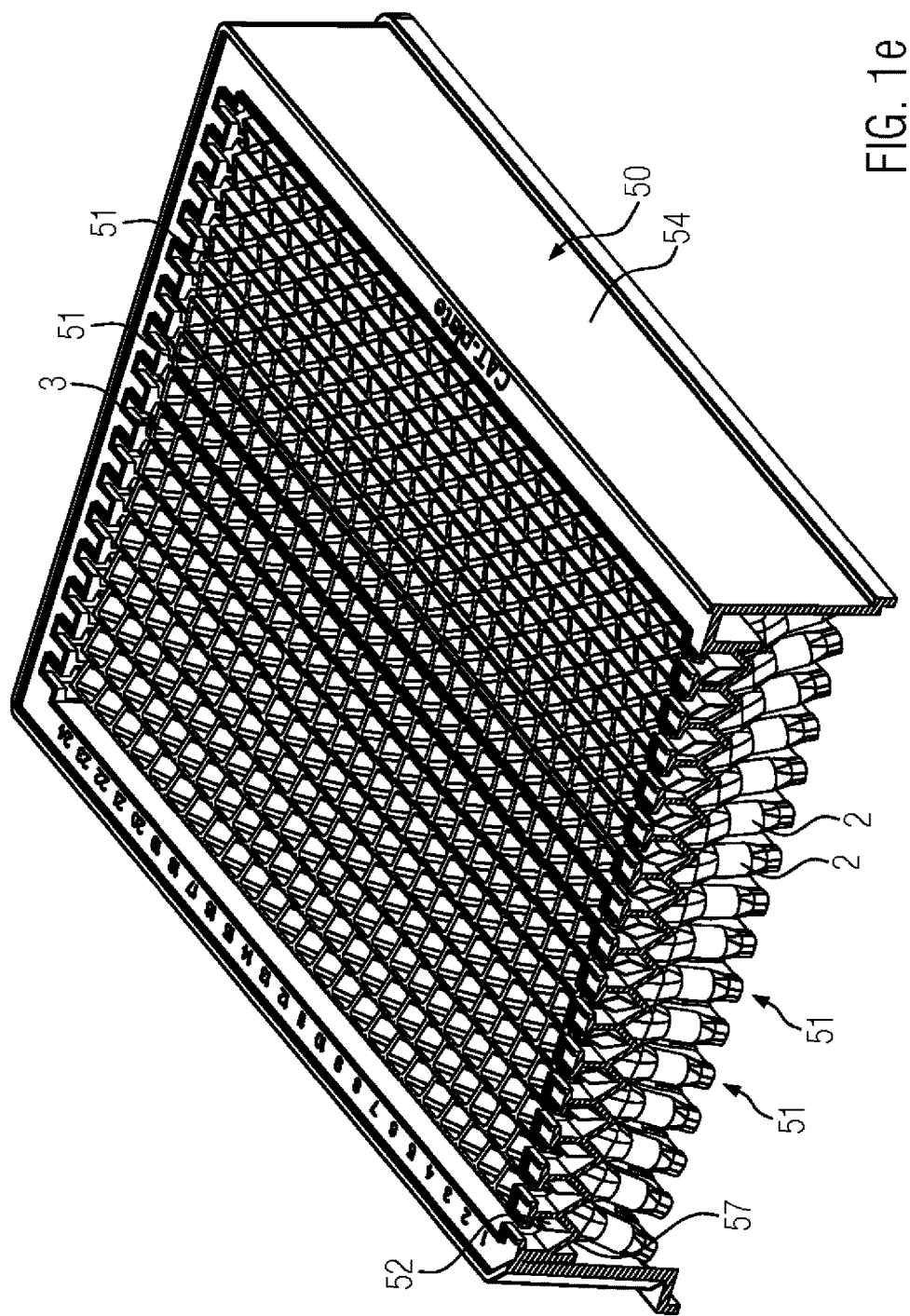
Figure 1F:
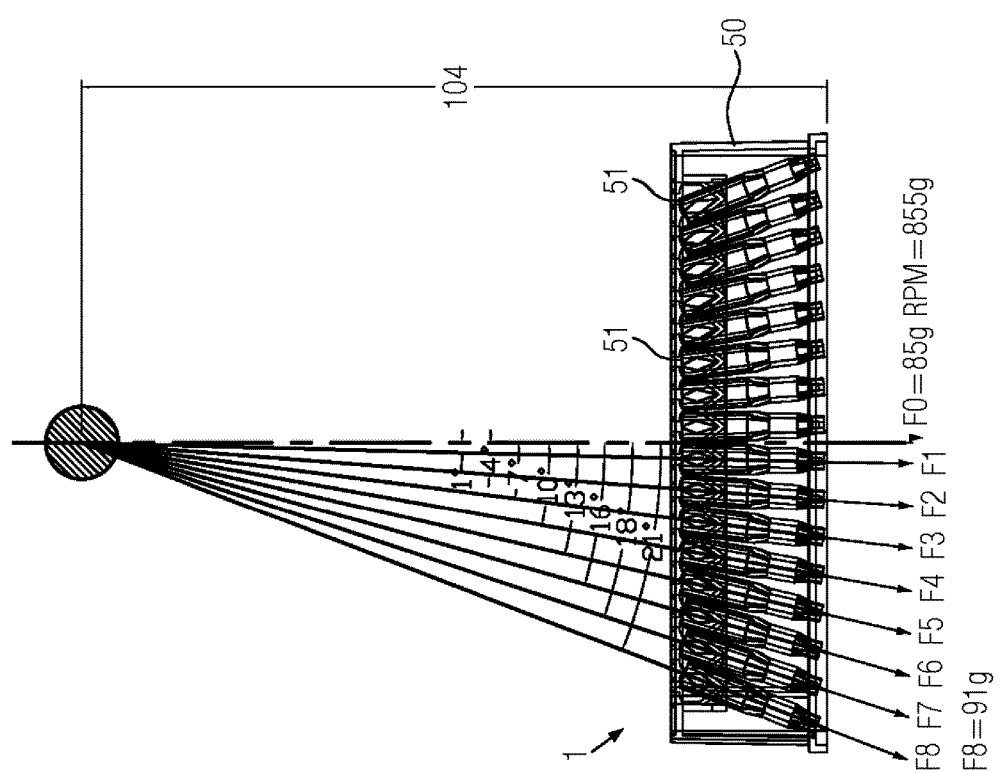
FIG. 1f is a schematic view of the rotating microplate and the corresponding rotation axis.

The struts 51 can be inclined or pivoted around a longitudinal axis extending along the tapered lower edges 53. When the microplate 1 is centrifuged then the reaction wells 2 align with the direction of the centrifugal force. FIGS. 1e and 1f show the microplate 1 in a partially cut perspective view, wherein the microplate is rotating around an axis 24, The rotation radius is denoted with an r. The struts 51 which are close to the longitudinal sidewalls 54 are tilted so that the bottom section of the reaction wells 2 is closer to the longitudinal sidewalls 54 than the openings 3 in the upper section of the reaction wells 2. The more the struts 51 are arranged closer to the middle in between the two longitudinal sidewalls 54, the smaller is the tilting angle. By this pivotable arrangement of the struts it is secured that during centrifuging the centrifugal force F1-F8 is aligned with the axis 61 of each reaction well 2. This secure that the centrifugal force is directed in each reaction well to the bottom of the reaction well 2 and not to a sidewall of the reaction well 2. Different materials in the reaction wells 2 form homogeneous layers which extend orthogonal to the axis 61 of the reaction wells. It is avoided that these layers are tilted with respect to the axis 61 of the reaction wells. Such tilted layer could cause problems in an automatic optical detection process.

The struts 51 are rigid in longitudinal direction so that they are not bending during centrifuging. In the present embodiment the struts 51 form a monolithic body, wherein intermediate wall sections 62 are provided as stiffening elements in the sections between neighboring reaction wells 2 where the reaction wells 2 are distant to each other (FIG. 1c, 1d).

A second embodiment of a microplate 1 comprises a frame 63 and an insert 64. The insert 64 defines a plurality of reaction wells 2 which are arranged in a two-dimensional array. The two-dimensional array comprises 16 rows of reaction wells 2, wherein each row comprises 24 reaction wells 2. Each row is substantially embodied as the struts 51 of the first example, wherein intermediate wall sections 62 are provided as stiffening elements in the sections between neighboring reaction wells 2 where the reaction wells 2 are distant to each other. However, each row of reaction wells 2 is connected with the neighboring row of reaction wells by a thin elastic strip 65. The insert 64 comprises a collar 66 which surrounds the array of reaction wells 2.

Figure 2B:
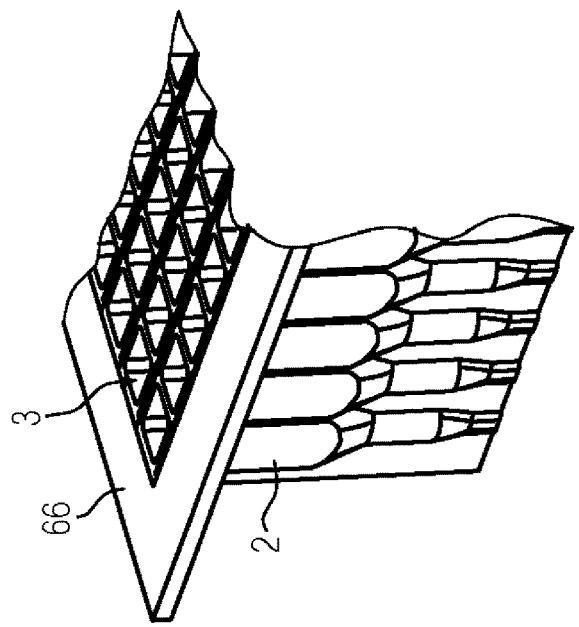
FIG. 2b is a partially cut perspective view of the insert of FIG. 2a, FIG. 2c is a perspective view of the microplate according to FIG. 2a wherein no centrifugal force is acting.
Figure 2A:
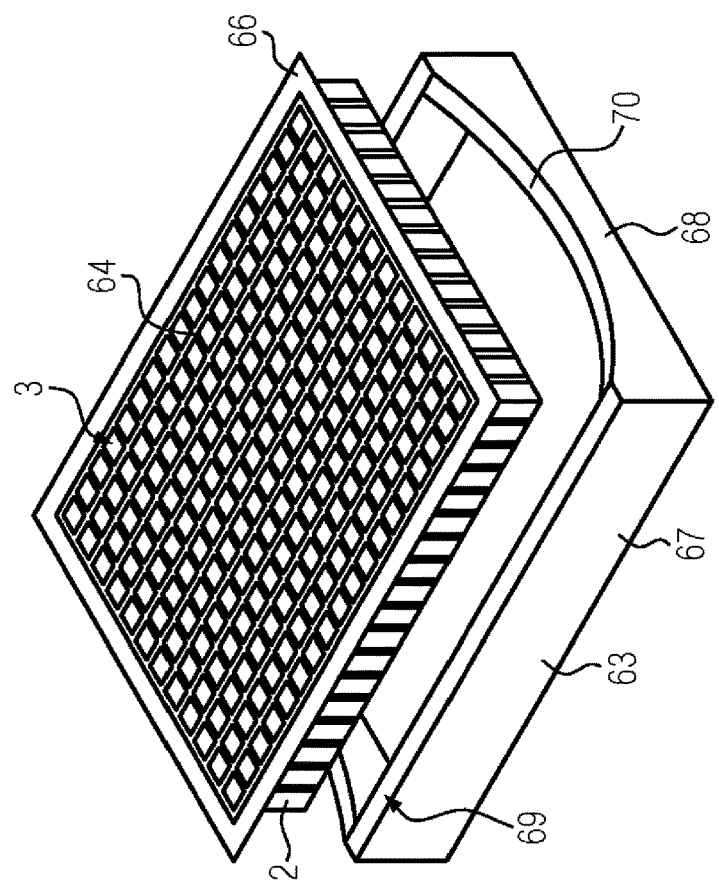
FIG. 2a shows a second embodiment of a microplate comprising a frame and a an elastic insert in a perspective explosion view.
Figure 2C:
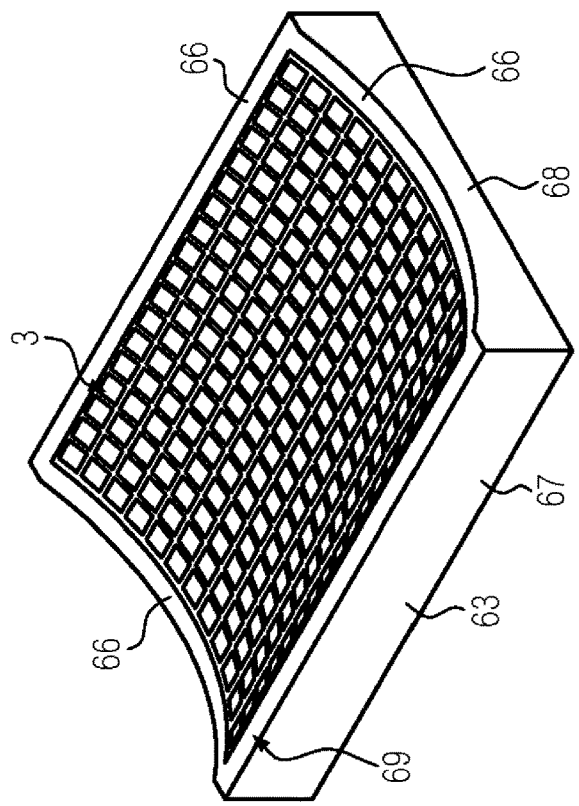
FIG. 2d is a perspective view of the microplate according to FIG. 2a wherein a centrifugal force is acting.
Figure 2D:
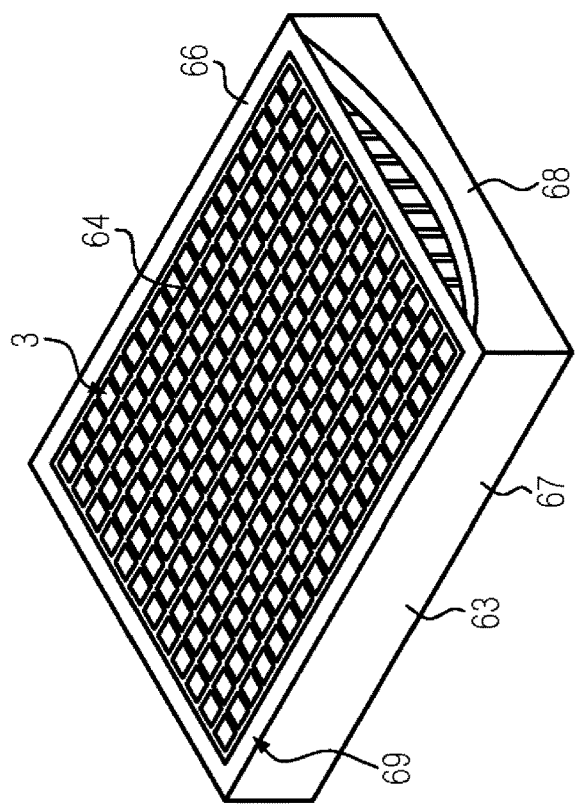
Figure 3A:
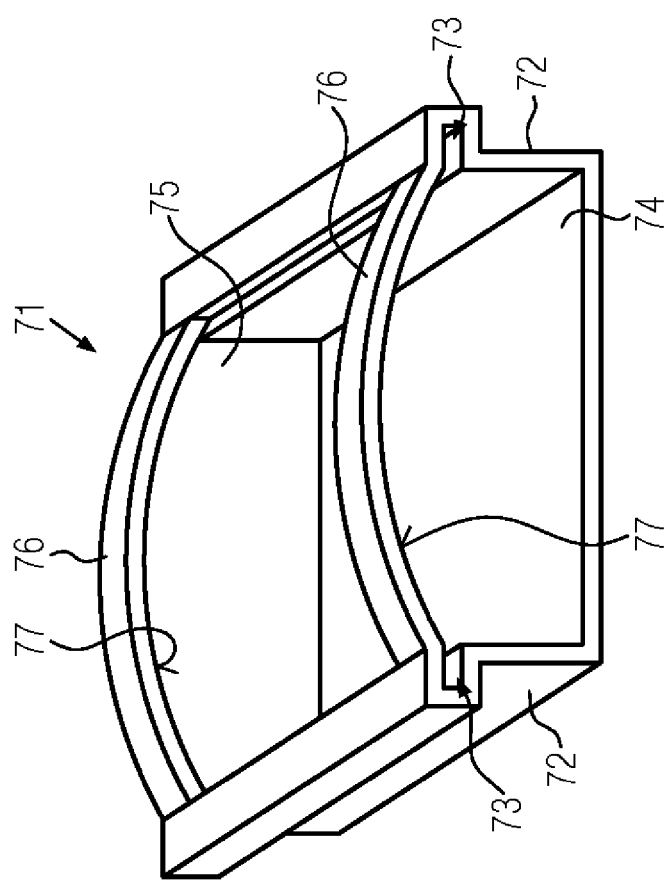
FIG. 3a shows a frame of a second embodiment of a microplate comprising a frame and a an elastic insert in a perspective view.
Figure 3B:
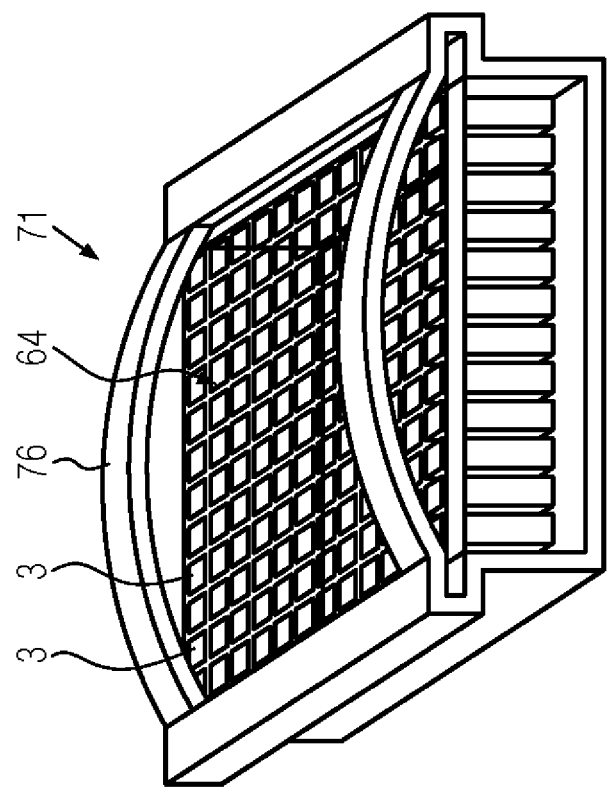
FIG. 3b is a perspective view of the frame according to FIG. 3a together with an insert wherein no centrifugal force is acting.
Figure 3C:
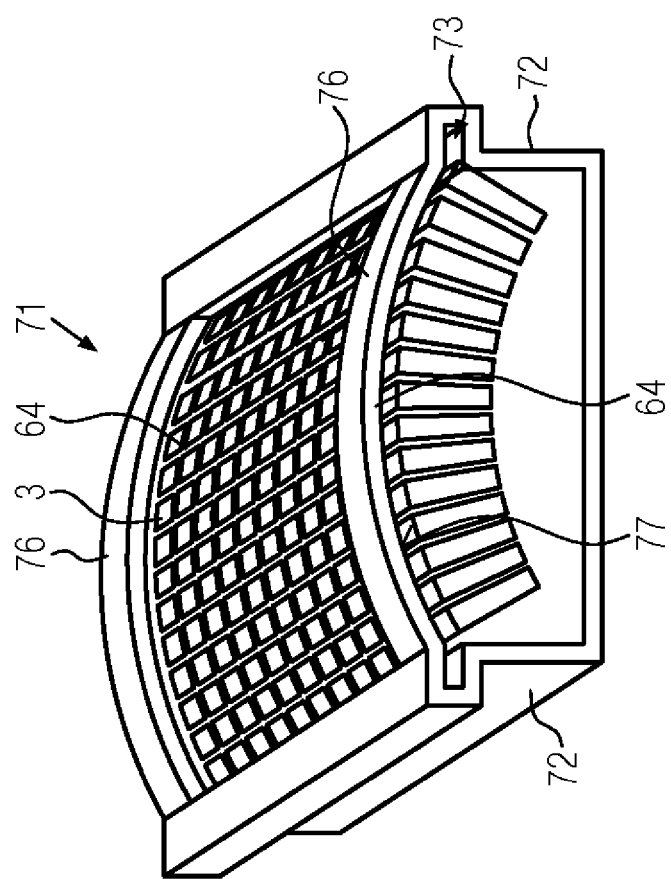
FIG. 3c is a perspective view of the frame according to FIG. 3a together with an insert wherein a centrifugal force is acting.

The frame 63 comprises two longitudinal sidewalls 67 and two lateral sidewalls 68. The longitudinal sidewalls 67 are embodied with a linear, horizontal upper edge 69. The lateral sidewalls 68 have an upper edge 70 which has a concave curvature. The insert 64 can be put into the frame 63 so that the collar 66 is supported by the linear upper edges of the longitudinal sidewalls 67 (FIG. 2c). When a centrifugal force is acting onto the insert 64 then the insert 64 is bent so that the collar 66 is abutting on the curved upper edges 70 of the lateral sidewalls 68. The curvature of the upper edges 70 of the lateral sidewalls 68 is so designed that the distant of each point on the upper edge 70 to a rotational axis of a centrifuge is substantially the same. Therefore, during centrifuging the insert 64 is bent in such a way that all reaction wells 2 are aligned with the direction of the centrifugal force. As the insert 64 is made of an elastic plastic material, the insert returns in the flat shape when no centrifugal force is acting anymore.

The insert 64 is flexible only around an axis parallel to the rows of the reaction wells but not around an axis which is directed in the direction of the columns of the reaction wells. In other words, the rows of reaction wells 2 are stiff in their longitudinal directions.

The microplate 1 according to the second embodiment provides the same advantages as the microplate 1 according to the first embodiment due to the alignment of the reaction wells with the direction of a centrifugal force.

The second embodiment can be modified with another frame 71, wherein the insert 64 maintains the same.

The frame 71 comprises two longitudinal sidewalls 72. The longitudinal sidewalls 72 are each formed to a longitudinal groove 73 at their upper edges. The grooves are diametral opposite to each other so that they open to the center of the frame 71. The frame has a bottom wall 74 and a rear wall 75. The front side of the frame 71 is open so that the insert can slide along the grooves 73 into the frame 71.

The front and the rear ends of the upper parts of the grooves 73 are connected by bows 76 which form a segment of a circle. The bows 75, 76 extend away from the bottom wall 74 so that the bows define curved lower edges 77. The bows 75, 76 and the upper parts of the groove form a frame-like element which surrounds the reaction wells comprising area of the insert.

When a centrifugal force is acting onto the insert 64 then the insert 64 is bent so that the collar 66 is abutting on the curved lower edges 77 of bows 75, 76. The curvature of the lower edges 77 of the bows 75, 76 is so designed that the distance of each point on the lower edges 77 to a rotational axis of a centrifuge is substantially the same. Therefore, during centrifuging the insert 64 is bent in such a way that all reaction wells 2 are aligned with the direction of the centrifugal force. As the insert 64 is made of an elastic plastic material, the insert returns in the flat shape when no centrifugal force is acting anymore.

The two versions of the second embodiment comprise each a frame and an insert. The special form of the frame can also be part of a tray of a centrifuge and the insert alone can form the microplate which can be put into the tray.

The second version of the second embodiment is provided for centrifuging the reaction wells with its openings directed outwardly. This is uses for washing and or cleaning the reaction wells.

In the above two embodiments of the microplate 1 the reaction wells are inclinable or pivotably arranged around an axis extending along the longitudinal direction of the rows of reaction wells. Basically, it is also possible to embody the microplate so that the reaction wells can be pivoted around an axis which is lateral to the longitudinal extensions of the rows of reaction wells. This pivoting axis should be parallel to a rotation axis of a centrifuge when the microplate is put into such a centrifuge for centrifuging. Thus, the direction of the pivoting axis depends how the microplate is placed in the centrifuge. Basically, it is advantageous if the pivoting axis is parallel to the longitudinal extensions of the rows of reaction wells, wherein the rows of reaction wells comprise more reaction wells in a two-dimensional array than columns of the array which are lateral to the rows. Thus, the longer extension of the array of reaction wells is preferably parallel to the rotation axis of the centrifuge.

Figure 4:
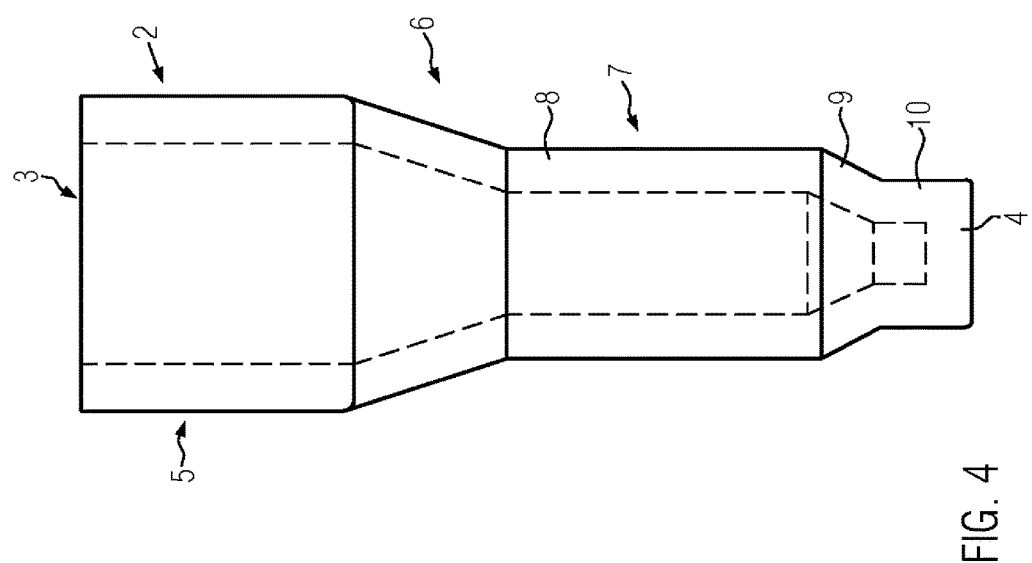
FIG. 4 is a side view of a single reaction well of one of the microplates according to FIGS. 1a to 2d, wherein the inner edges are depicted in dashed lines.

Each well 2 (FIG. 4, 5) is identical. Each reaction well 2 has the opening 3 at its top end and a bottom wall 4 at its bottom end. In the intended use, the microplate is arranged with the openings directed upwards and the bottom walls directed downwards. Therefore, in the following description the term upwards is used as being directed to the opening 3 and the term downwards is used as being directed to the bottom wall 4.

The reaction well 2 comprises a filling section 5 at the top end. The filling section 5 has a cross-sectional area in the form of a square. Of course, other cross-sectional forms as circles or rectangles are possible. However, the form of a square is preferred because this allows the largest cross-section area for an arrangement with a certain density of reaction wells 2 per area. The larger the cross-section area of the filling section 5 is, the easier it is to fill the reaction well 2.

A transfer section 6 is provided below the filling section 5 which joins the filling section 5 with a separation section 7. The separation section 7 comprises a smaller cross-sectional area than the filling section 5, so that the transfer section 6 is downwardly tapered to provide a transfer from the larger cross-section area of the filling section to the smaller cross-sectional area of the separation section 7.

The separation section 7 comprises an upper part 8 in the form of a hollow cylinder. In the present embodiment, the upper part 8 has a cross-sectional area in the form of a square.

A lower part 9 of the separation section 7 is embodied as a conical portion which is tapered downwards.

The lower end of the conical portion 9 leads to a collection section 10. The collection section 10 is embodied in the form of a hollow cylinder. This hollow cylinder has a circular cross-sectional area in the present embodiment.

The cross-sectional area of the collection section 10 is substantially smaller than the cross-sectional area of the upper part 8 of the separation section 7. The lower part or conical portion 9, respectively, reduces the cross-sectional area on the upper part 8 of the separation section 7 to the collection section 10 in a ratio of at least 2:1, preferably at least 3:1 and particularly preferably at least 4:1.

A major part of the separation section is filled with the separation material, such as a gel material or a bead matrix. Such separation material is used for separating agglutinated sample parts from non-agglutinated sample parts. If agglutinated and non-agglutinated parts of a sample material are provided on the top side of the separation material and are submitted to a centrifugal force directed from the top and to the bottom end of the reaction well 2, then only the non-agglutinated parts of the sample penetrate a gel material or a filter material, such as a bead matrix. Thus, it is possible to separate agglutinated sample parts from non-agglutinated sample parts and to collect non-agglutinated sample parts in the collection section.

Due to the reduction of the cross-sectional area with respect to the upper part 8 of the separation section 7 to the collection section 10, the penetrating parts of the sample material are concentrated to the center of the reaction well. Thus, the penetrating parts of the sample material are concentrated in the small volume of the collection section 10. As a result, the collection section 10 comprises a high concentration of sample material penetrated through the separation material. Such a high concentration of sample material is advantageous for optical detection.

In the present embodiment, the height of the filling section is 4.5 mm, the height of the transfer section 6 is 3 mm, the height of the upper part 8 of the separation section 7 is 5 mm, the height of the conical portion 9 of the separation section 7 is 1 mm and the height of the collection section 10 is 1 mm.

The length of the outer edges of the filling section 5 is 4.5 mm. The wall thickness of the reaction well is about 0.7 mm.

The length of the horizontal inner edges of the upper part 8 of the separation section 7 is about 2 mm, so that the cross-sectional area of the upper part 8 of the separation section 7 is about 4 mm$^2$. The diameter of the cross-sectional area of the collection section 10 is not larger than 1 mm, so that the cross-sectional area is smaller than 1 mm$^2$.

The total inner height of the reaction well 2 which extends from the inner side of the bottom wall 4 to the top end of the reaction well 2 is 14.5 mm.

The above given numbers describe a specific example of a reaction well 2. Of course, it is possible to vary the dimensions. If the microplate 1 comprises a lower number of reaction wells 2, the cross-sectional areas of each reaction well 2 can be enlarged for a microplate with the same size.

In dependence of the kind of separation material which is used, the dimension of the height of the separation section 7 can be varied. A major part of the separation section 7 is filled with the separation material. It is also possible that the transfer section 6 and even a lower portion of the filling section 5 is filled with separation material.

As it can be seen in FIGS. 1c and 1d, the walls defining the filling section 5 are each part of two reaction wells 2 on either side of these walls.

Figure 6:
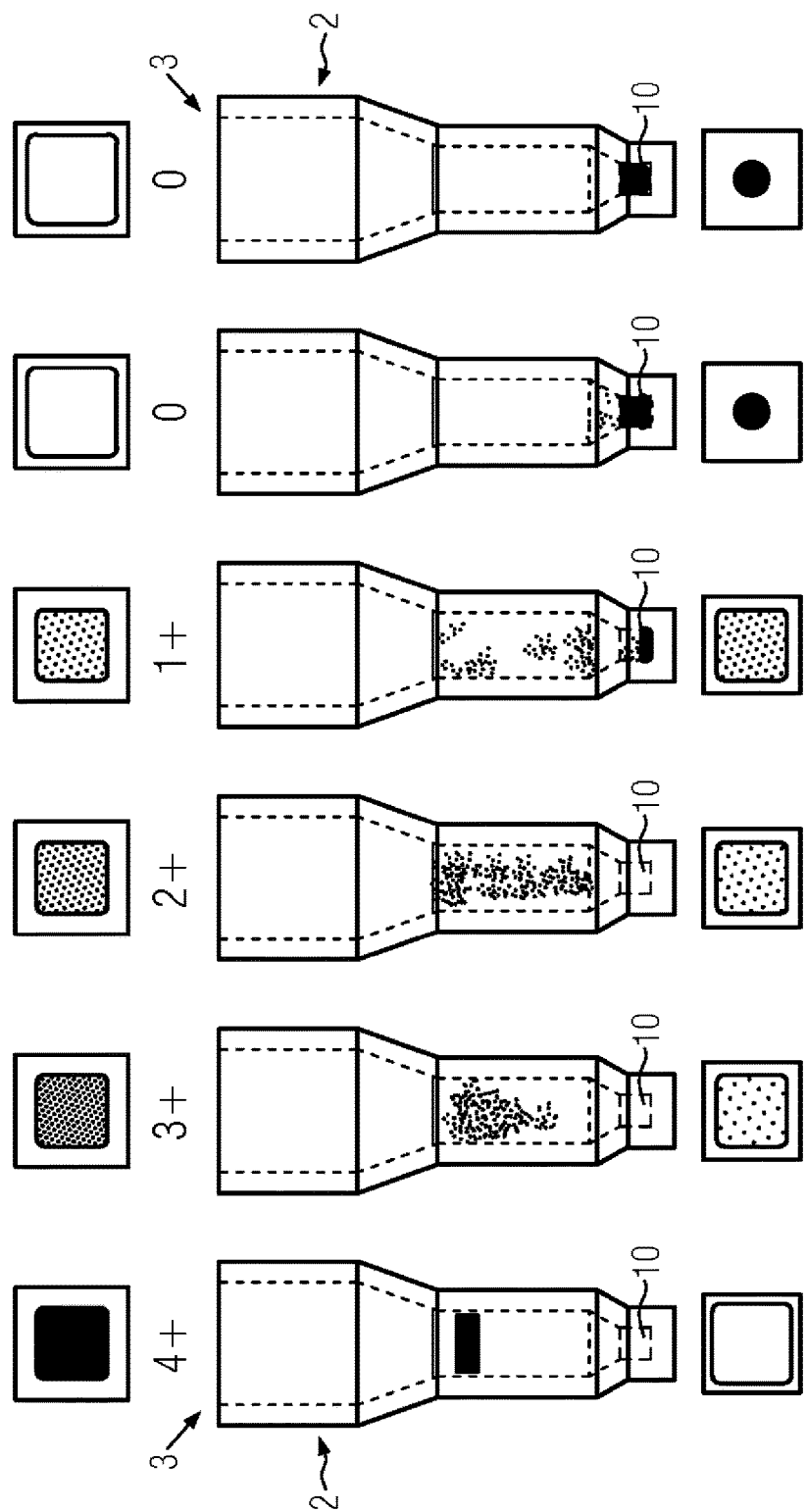

FIG. 6 shows a testing apparatus 13 for determining the result of an agglutination reaction.

Figure 8:
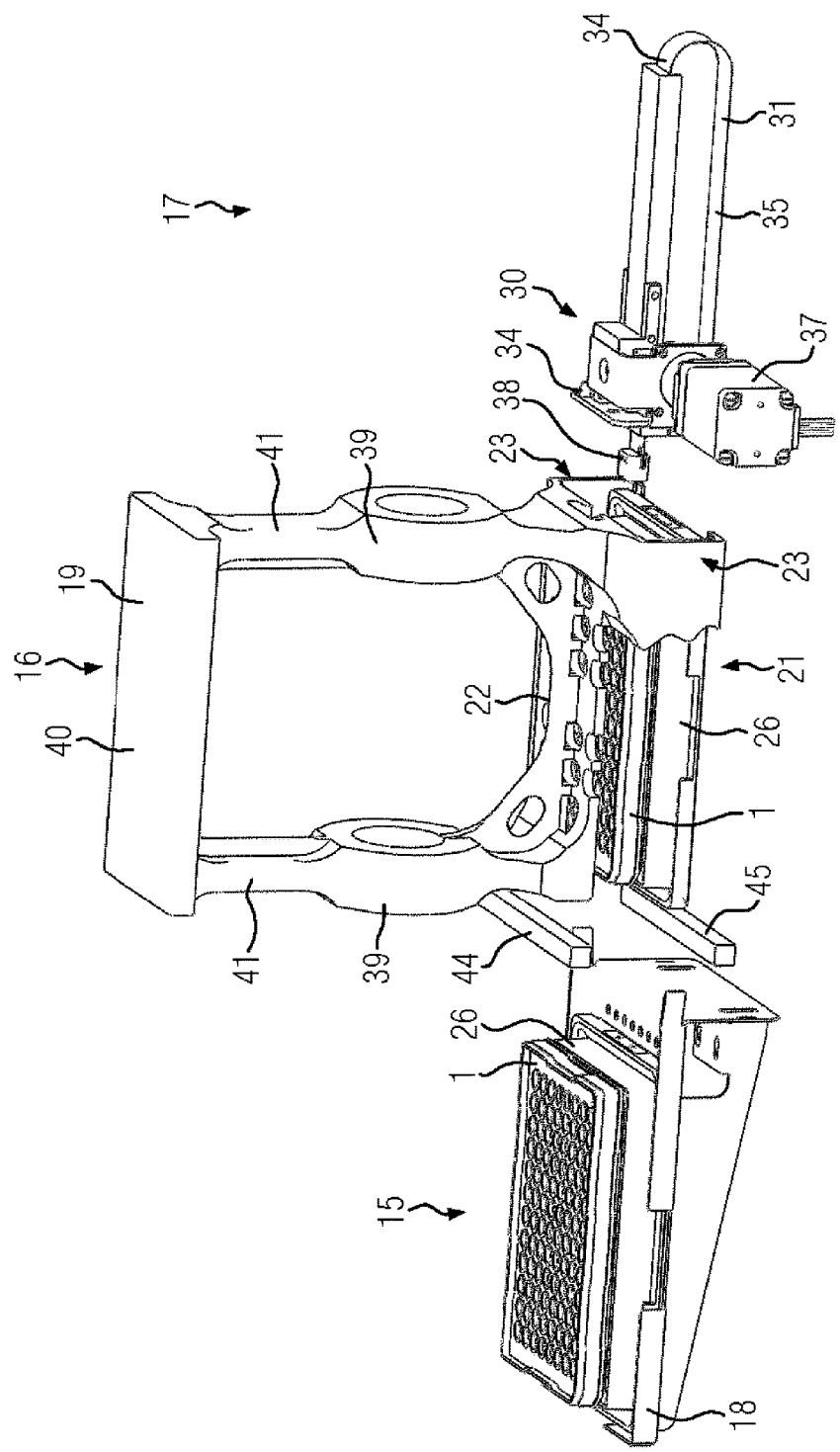

The centrifuge 14 comprises a front platform 15, a centrifuge section 16 and a driving section 17 (FIG. 8, 9, 10).

The front platform 15 has, in the top view, a rectangular form which is slightly larger than a standard microplate. Rims 18 are provided on all side edges of the front platform 15 except the one adjacent to the centrifuge section 16.

Figure 9:
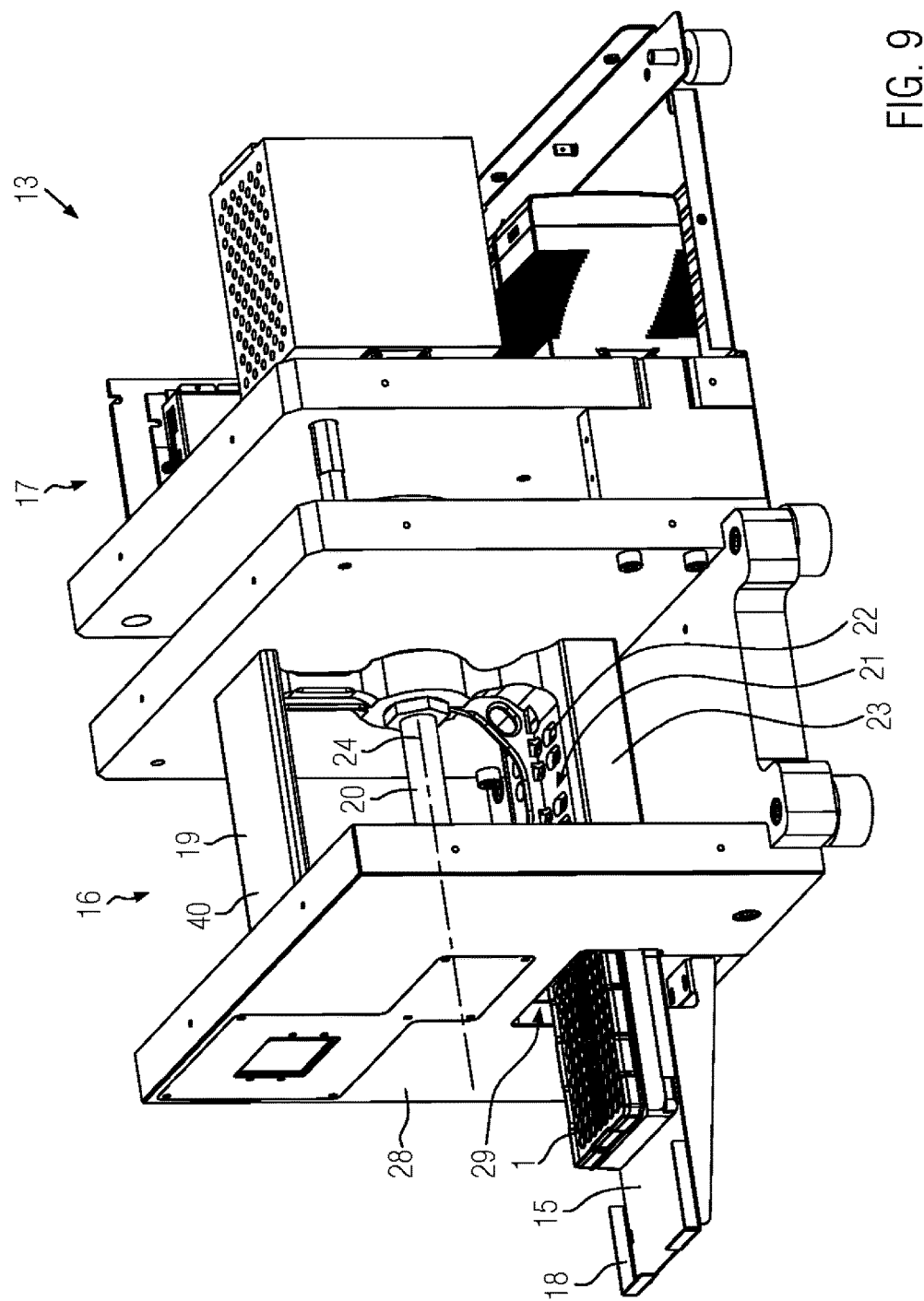
Figure 10:
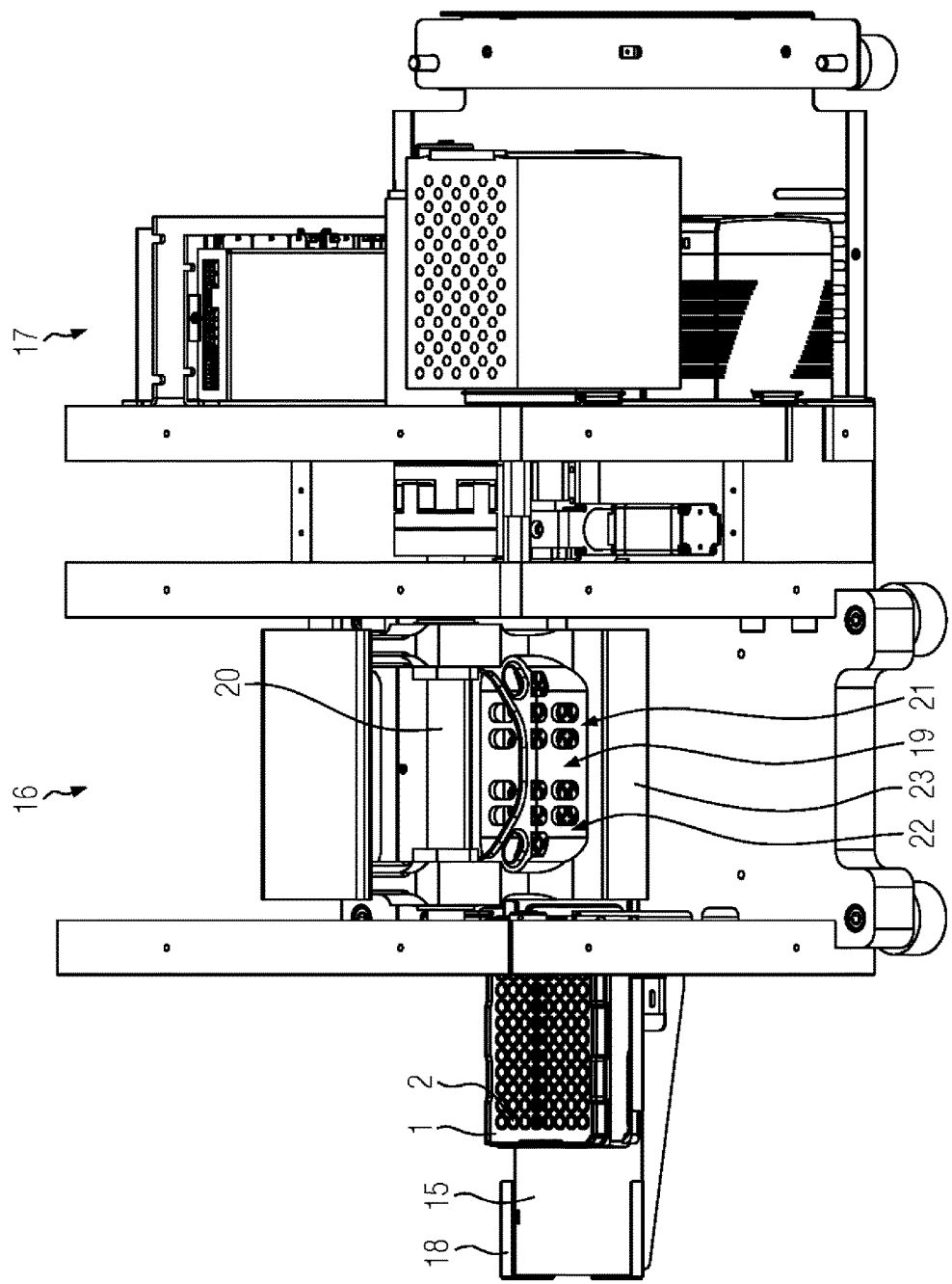
Figure 11:
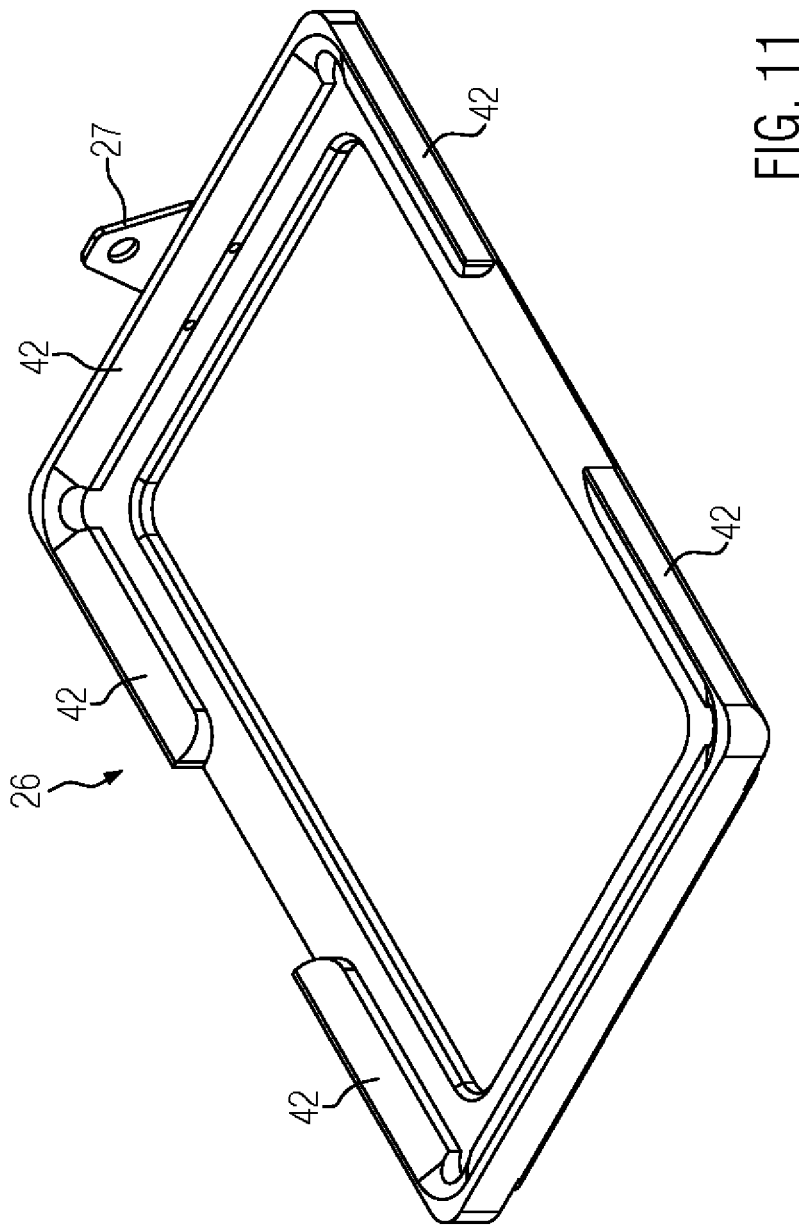

The centrifuge section 16 comprises a rotor 19. The rotor 19 is mounted on a horizontal shaft 20 (FIG. 9). The rotor 19 comprises a receptacle section for receiving one microplate 1. The receptacle section is embodied as plate tray 21. The plate tray 21 is defined by a rectangular base wall 22 and two U-rails 23. The U-rails 23 are arranged opposite with their open sides. In the lowest position of the plate tray, the U-rails 23 are below the base wall 22. In FIG. 8 the plate tray 21 is partly cut out, so that the microplate 2 and the microplate carrier 26 (FIG. 11) held in the plate tray 21 are visible.

The distance of the plate tray 21 to the rotation axis 24, which is the radius r of rotation, can be freely chosen. It is preferably in the range of 1 time to 2 times of the lateral extension of the microplate 1.

Diametrically opposite to the receptacle section or plate tray 21, a counterweight 40 is fixed to flanges 39 by means of legs 41. A further plate tray could be provided instead of a counterweight 40, which is embodied for receiving a microplate or a microplate carrier together with a microplate to form an adjustable counterweight to the kind of microplate used in the plate tray 21.

An opening 29 in a front side wall 28 is embodied at the level of the lowest position of the plate tray 21, which is the loading position of the rotor 19. The front platform 15 is provided on the same level as the base wall 22 of the plate tray 21 in the loading position, so that a microplate or a microplate on a microplate carrier can slide from the front platform 15 onto the base wall 22 and vice versa, wherein the openings of the reaction well 2 of the microplate 1 are directed to a shaft 20 which holds the rotor 19.

In the present embodiment, the base walls 22, the U-rails 23 and the sections in between the base walls 22 are made from one single piece of aluminium.

On the front side of the rotor 19, the plate trays 21 are open so that a microplate can slide into the plate tray 21. At the rear side of the rotor 19, a stopper 25 is provided. The stopper 25 comprises preferably a magnetic element.

The section in between the base walls 22 is cut out as far as possible and bores are provided in the base walls 22 to minimize the moment of inertia.

In the present embodiment, the plate tray 21 is designed for receiving a microplate 1 together with a microplate carrier 26. The microplate carrier 26 (FIG. 11) is a rectangular frame having rims 42 at the side edges, wherein the inner surfaces of the rims define the position of a microplate on the microplate carrier 26 with a small play. The upper surfaces of the rims 42 are tilted inwardly so that a microplate is sliding into the section which is defined by the rims.

The microplate carrier 26 comprises at one side edge a coupling element 43 made of magnetic material, particularly of a ferromagnetic material. This coupling element 27 can cooperate with the magnetic stopper 25 on the rotor 19.

The opening 29 in front side wall 28 has the form of a rectangular slid. An automatic door is provided for closing the opening 29. The opening 29 is arranged in the level of the front platform 15. In the loading position, the rotor 19 is arranged horizontally with its base walls 22, wherein the base wall of the plate tray 21 is arranged on the same level as the front platform 15, so that a microplate carrier 26 and a microplate 1 can slide horizontally from the front platform 15 into the lower plate tray 21 and vice versa.

On the upper edge of the opening, pipetting nozzles are provided for dispensing reagents into the reaction wells 2 of the microplate 1.

Figure 7:
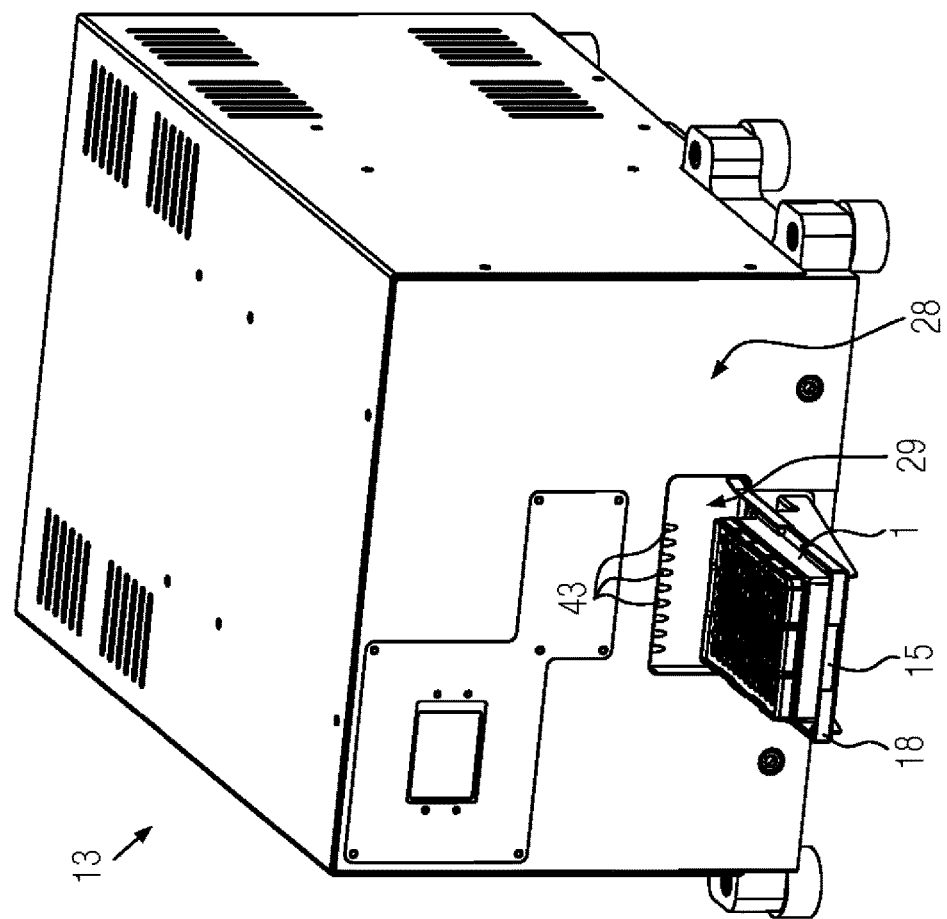

In the gap between the front platform 15 and the rotor 19, an upper line camera 44 is disposed above the transportation path of the microplate with its viewing direction downwards onto the top surface of the microplate 1. A lower line camera 45 is disposed below the transportation path of the microplate with its viewing direction upwards onto the bottom surface of the microplate 1 (FIG. 7). When the microplate 1 is moved through the opening 29, images of the complete upper and lower sides of the microplate 1 can be detected by the line cameras 44, 45.

The driving section 17 comprises a motor (not shown) for rotating the shaft 20 and the rotor 19. The motor is connected to a control unit for controlling the rotation speed. This centrifuge is designed for centrifuging a microplate 1. As the distance between the microplate and the shaft 20 or rotation axis 24 is large, nearly the same centrifugal acceleration is exerted to the fluid in the different reaction wells 2. Therefore, the same centrifugation effect is achieved independently of whether the fluid is located in a center reaction wells or a lateral reaction well.

A control unit is provided to control the speed as well as the acceleration of the rotor. The speed of the rotor is in the range of 100 RPM to 3,000 RPM. The acceleration and deceleration of the rotor lies in the range of 100-1,200 RPM/s. When starting the rotor, it shall be accelerated, so that, after a turn of about 180°, at least a centrifugal acceleration of 1 g should be applied, so that no fluid drops out of the reaction wells with its openings directing downwardly. Microplates having deep well reaction wells can be accelerated as fast as possible. However, accelerating microplates with small wells as reaction wells could cause a contamination by sloshing of fluid from one reaction wells to a neighboring reaction well due to the acceleration. The danger of such a sloshing contamination depends on the filling amount of the reaction wells as well as on the form of the reaction wells. It has been shown that with an acceleration up to 500 RPM/s to 1,200 RPM/s, no contamination due to sloshing occurs.

The driving section 17 also comprises a loading mechanism 30 for loading and unloading the centrifuge 14 with a microplate 1.

A loading mechanism 30 comprises a flexible elongated beam 31 for extension and retraction of a microplate 1 or a microplate carrier 26 together with a microplate 1 (FIG. 7). The flexible elongated beam 31 is made of a stripe of metal sheet which is slightly bent transverse to its longitudinal extension. Thus, the metal sheet provides certain stiffness if it is extended linearly and on the other hand it can be bent around an axis transverse to the longitudinal extension. Such bent metal sheet stripes are well known from metal measuring tapes.

In the present embodiment, one end of the beam 31 is fixed vertically at an inner wall 32 of the driving section 17, wherein the beam is extending from the inner wall 32 rearwards. The beam 31 is bent by a U-turn, so that a free end 33 of the beam is directed forwardly and the beam is extending through a slid in the inner wall 32. Thus, the beam comprises an upper strand 34 fixed to the inner wall 32 and a lower strand 35 extending through the slid of the inner wall 32. The strand 35, which is extending through the inner wall 32 and which comprises the free end 33, is clamped between two wheels (not shown), wherein one of the two wheels is driven by a stepper motor 37. Only one of the two wheels is shown in the drawings. The free end 33 of the beam 31 is provided with a magnetic element 38. The beam 31 can be actuated by means of the stepper motor 37 so that the free end 33 with its magnetic element 38 is extended or driven through the centrifuge section 16 and through the opening 29 in the front side wall 28. Thus, the free end 33 of the beam 31 reaches the area of the front platform 15 in the maximum extended position. In the maximum retracted position, the free end 33 of the beam 31 is arranged behind the rotor 19 and particularly out of the centrifuge section 16, so that the rotor 19 can be freely rotated.

The loading mechanism 30 can be coupled to a microplate carrier 26, which is placed on the front platform 15, just by extending the beam 31 until the magnetic element 38 of the beam couples through the coupling element 27 of the microplate carrier 26. By retracting the beam 31, the microplate carrier 26 is drawn into one of the plate trays 21 of the rotor 19. When the microplate carrier 26 abuts to the stopper 25, the coupling between the magnetic element 38 of the beam 31 and the coupling element 27 of the microplate carrier 26 is released by further retracting the beam and simultaneously the coupling element 27 of the microplate carrier 26 is coupled to the magnetic element of the stopper 25 and thus fixed in position in the rotor 19.

This loading mechanism 30 allows coupling the centrifuge 14 to any transport system for transporting microplates in an automatic labor robot. The labor robot just has to put a microplate 1 onto a microplate carrier 26 located at the front platform 15. Then the loading mechanism 30 can load and unload the rotor 19. It is also possible to place the centrifuge 14 without a front plate directly adjacent to a transport belt for transporting microplates, wherein microplates 1 can be withdrawn from the transport belt with the loading mechanism 30 and can be put onto the transport belt again. In the present embodiment, a microplate carrier 26 having a coupling element 27 is used. It is also possible to provide the microplates 1 with such coupling elements 27, so that there is no need for a microplate carrier.

A further advantage is that the loading mechanism 30 is placed on the rear side of the centrifuge section 16, so that the centrifuge 14 can be coupled to an existing laboratory robot without any intermediate devices. This facilitates the integration of the centrifuge into existing laboratory robots.

In the following, the use of the above-described microplate 1 in the testing apparatus 13 is described for determining the result of one or more agglutination reactions.

The method starts preferably with an empty microplate 1. The reaction wells 2 are filled by means of a pipetting device with a gel material. For each agglutination reaction which is to be carried out, an individual reaction well 2 is filled with gel material. If the number of agglutination reactions is smaller than the number of reaction wells 2 provided in one microplate, then the reaction wells which are not needed are not filled with gel material.

After filling the respective reaction wells with each a specific amount of gel material, the microplate is centrifuged to force the gel material to the lower portion of the reaction wells, so that the gel material fills the collection section and a major part of the separation section 7 without containing any air bubble.

Due to the centrifugation step, it is possible to fill the reaction wells on site with gel material, even if reaction wells with small diameter are used. There is no need for reaction wells which are preloaded with separation material. Of course, it is also possible to use preloaded reaction wells.

The reaction wells containing separation material are loaded with a suspension containing a specific reagent. Different reaction wells can be loaded with different reagents. The reagents typically comprise an antigen or antibody or blood cells of a known blood type.

A certain amount of a sample under test is dispensed in the reaction wells containing the separation material and the reagent. Preferably, the sample material of the same sample is distributed to reaction wells containing different reagents and material of different samples can be distributed to different groups of reaction wells. Thus, it is possible to simultaneously test a plurality of different samples, wherein each sample is tested with respect of a plurality of different reagents.

The microplate containing reaction wells loaded with samples, reagents and separation material is incubated, wherein a certain temperature is applied for a predetermined duration. This incubation step can be carried out in a separate incubator. Optionally, the centrifuge comprises a heating means, so that the microplate can be incubated in the centrifuge. Thereafter, the microplate is centrifuged, wherein the non-agglutinated sample parts penetrate the gel material in the direction to the bottom wall 4 of the reaction wells 2. The non-agglutinated parts of the sample are collected in the collection section 10 of the reaction wells 2. If the result of the agglutination reaction is that an agglutination took part, then the agglutinated sample material maintains on the top side of the separation material (FIG. 6*a*). If there is only a weak agglutination reaction or a retarded agglutination reaction, then agglutinated clumps are small and are stopped inside the gel-material and do not reach the bottom wall 4 or the collection section 10 of the reaction wells 2.

Figure 5:
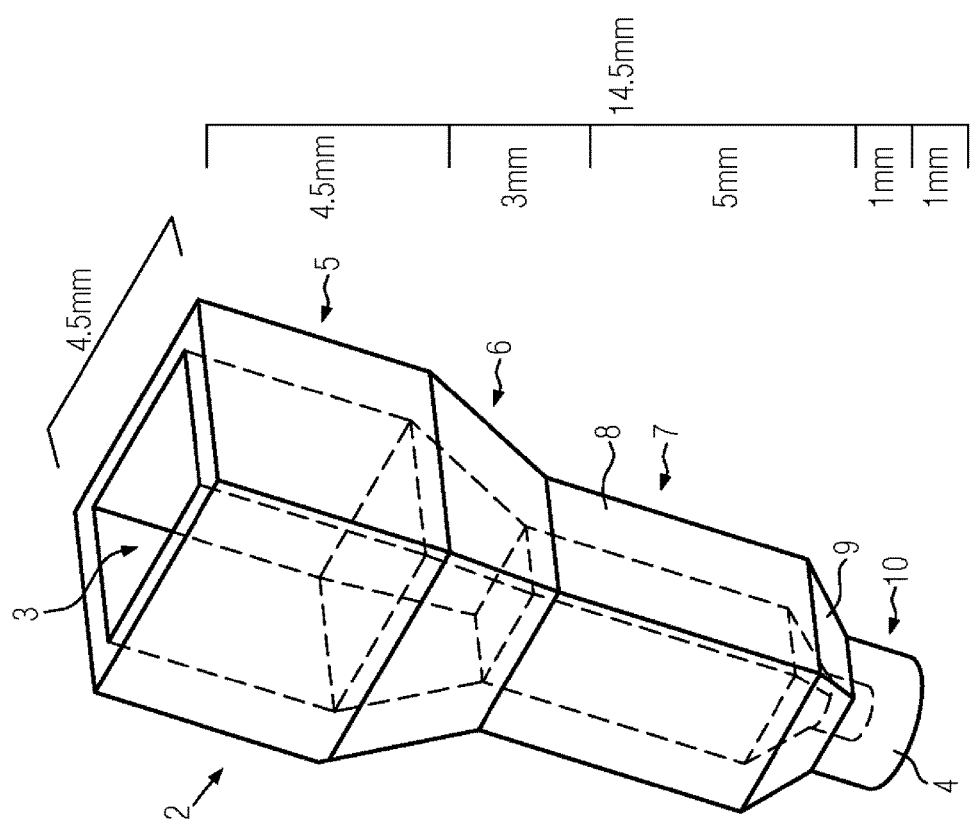
FIG. 5 is a perspective view of a single reaction well of one of the microplates according to FIGS. 1a to 2d, FIGS. 6a-6f each reaction well containing a sample after carrying out the agglutination reaction and comprising each a picture of the well of the top side (above the well) and of the bottom side (below the well), FIG. 7-10 an apparatus for carrying out a method for determining the result of an agglutination reaction in different views without housing, and FIG. 11 a microplate carrier

The agglutinated gel material is retained in the gel material and distributed therein, as it can be seen in FIGS. 5*b* and 5*c*. The weaker the agglutination reaction is, the larger is the number of non-agglutinated sample parts and the more sample parts reach the collection section 10, as it can been in FIG. 5*d*-5*f*.

After the centrifugation step, the microplate is discharged from the centrifuge, wherein images are taken from the top side and the bottom side of the reaction wells with the line camera.

The FIGS. 6*a*-6*f* each show a picture of the top side above the respective reaction well 2 and a picture of the bottom side below the respective reaction well. The gray levels of these two pictures are automatically compared, wherein the difference of the gray levels is calculated. There are five classes of results, namely 0, 1+, 2+, 3+, and 4+. Each level of difference is assigned to a certain class, wherein if there is only agglutinated sample material, then the top side of the reaction well is dark and the bottom side of the reaction well is light and the corresponding class is 4+ and if the agglutination reaction is very weak, then all or nearly all sample parts reach the collection section 10 and the bottom side of the reaction well is dark and the top side is light (FIG. 6*f*), wherein the class is 0 (=no agglutination reaction).

If the sample material comprises red blood cells, then preferably color images are taken and the color intensity of the color red of the image of the top side and the bottom side are compared.

In the present embodiment, the cross sectional area of the opening 3 of the reaction well 2 has the form of a square and the collection section 10 has the cross sectional form of a circle. Thus, the pictures taken from the top side show a square and the pictures taken from the bottom side show a circle. By the form of the detected pattern (circle or square), it can be judged whether the picture is from the top side or the bottom side of the reaction well. These different forms of the cross sections of the upper and lower parts of the reaction wells ensure that, if the pictures are manually controlled, the pictures of the bottom side and the top side are not mixed with each other. Therefore, it is preferable that the forms of the opening 3 and the collection section 10 of the reaction wells 2 differ.

The absolute color intensities or gray levels depend on a plurality of circumstances, such as background light, type of separation material, amount of sample material dispensed into each reaction well, etc. By comparing the images of the top side and the bottom side of the reaction wells, these influences are eliminated, because the decision whether there is an agglutination reaction or whether there is no agglutination reaction is only based on the difference of the color intensity and/or gray level of the two images. This makes the test very reliable and stable. Furthermore, it is easy to calibrate the tests on different separation materials and different reagents, so that the overall process is very flexible. This system is particularly suitable for testing huge amounts of samples with a high throughput and at low costs.

In the above described embodiment, the color intensities and/or gray levels of the two images of the top side and the bottom side of the reaction well are compared. Additionally, the images can be compared with predetermined sample images.

In the above example a microplate having inclinable or pivotably arranged reaction wells is used in a method for determining the result of an agglutination reaction. The microplate with inclinable arranged reaction wells can be used for centrifuging any kind of samples. These microplates allow to simultaneously centrifuge a large number of different samples, wherein in each reaction well a correctly layered centrifugate is achieved. This is also achieved if the radius of rotation r is small.

What is claimed is:

1. Microplate comprising a plurality of wells arranged in a two-dimensional array, wherein the microplate comprises a frame and several longitudinal struts each comprising a row of wells, wherein the struts are independently pivotably arranged in the frame, wherein each row of wells is inclinably mounted in the microplate so that the axis of each well aligns with the direction of a centrifugal force during centrifuging of the microplate.

2. Microplate according to claim 1,
wherein the wells are elastically inclinable arranged in the microplate.

3. Microplate according to claim 1,
wherein at least one of said wells contains a separation material such as a gel or a bead matrix.

4. Microplate according to claim 2,
wherein at least one of said wells contains a separation material such as a gel or a bead matrix.

5. Microplate according to claim 1,
wherein at least one of said wells comprises a separation section which contains a separation material such as a gel or a bead matrix,
wherein the separation section comprises at least one conical portion which is tapered downwards, so that sample material penetrating the separation material will be concentrated to the center of the respective well, and wherein the wells comprise preferably a collection section for collecting the sample material penetrating the separation material at a bottom end of the well, wherein the collection section has preferably the form of a hollow cylinder, and/or wherein the separation section comprises a hollow cylinder.

6. Microplate according to claim 4,
wherein at least one of said wells comprises a separation section which contains a separation material such as a gel or a bead matrix,
wherein the separation section comprises at least one conical portion which is tapered downwards, so that sample material penetrating the separation material will be concentrated to the center of the respective well, and wherein the wells comprise preferably a collection section for collecting the sample material penetrating the separation material at a bottom end of the well, wherein the collection section has preferably the form of a hollow cylinder, and/or wherein the separation section comprises a hollow cylinder.

7. Microplate according to claim 1,
wherein the wells comprise a filling section at the top end of the wells, wherein the cross sectional area of the filling section is larger than the cross sectional area of the lower sections of the wells.

8. Microplate according to claim 6,
wherein the wells comprise a filling section at the top end of the wells, wherein the cross sectional area of the filling section is larger than the cross sectional area of the lower sections of the wells.

9. Microplate according to claim 1,
wherein the microplate comprises at least 96 wells, and/or,
wherein the inner height of the reaction wells is between 5 mm and 20 mm.

10. Microplate according to claim 8,
wherein the microplate comprises at least 96 wells, and/or,
wherein the inner height of the reaction wells is between 5 mm and 20 mm.

11. Microplate according to claim 10,
wherein the microplate comprises a frame and several longitudinal struts each comprising a row of wells, wherein the struts are pivotably arranged in the frame.

12. Microplate according to claim 1, wherein each strut comprises at its ends a mounting pin, wherein the mounting pins are arranged in an upper section of the struts and form a mounting element for a pivotably mounting of the struts in the frame.

13. Microplate according to claim 11,
wherein each strut comprises at its ends a mounting pin, wherein the mounting pins are arranged in an upper section of the struts and form a mounting element for a pivotably mounting of the struts in the frame.

14. Microplate according to claim 12,
wherein the frame comprises recesses for mounting the mounting pins of the struts.

15. Microplate according to claim 13,
wherein the frame comprises recesses for mounting the mounting pins of the struts.

16. Microplate according to claim 1,
comprising a frame and an insert, wherein the insert comprises the plurality of reaction wells which form a two-dimensional array and the frame has at least one supporting section, which has a concave curvature for supporting the insert during centrifuging of the microplate.

17. Microplate according to claim 11,
comprising a frame and an insert, wherein the insert comprises the plurality of reaction wells which form a two-dimensional array and the frame has at least one supporting section, which has a concave curvature for supporting the insert during centrifuging of the microplate.

18. Microplate according to claim 16,
wherein the frame comprises two supporting sections each provided for supporting an edge section of the insert.

19. Microplate according to claim 17,
wherein the frame comprises two supporting sections each provided for supporting an edge section of the insert.

20. Microplate according to claim 1,
wherein the microplate is made of an elastically deformable material.

21. Microplate according to claim 19,
wherein the microplate is made of an elastically deformable material.

22. Method for centrifuging a plurality of samples,
wherein the samples are contained in wells of a microplate, which is preferably embodied according to claim 1, wherein during centrifuging the wells align to the direction of the centrifugal force.

23. Method for centrifuging a plurality of samples,
wherein the samples are contained in wells of a microplate, which is preferably embodied according to claim 21, wherein during centrifuging the wells align to the direction of the centrifugal force.

24. Method according to claim 22,
wherein the microplate is rotated around a horizontal axis, and/or after centrifuging the samples are automatically optically detected.

25. Method according to claim 23,
wherein the microplate is rotated around a horizontal axis, and/or after centrifuging the samples are automatically optically detected.

26. Method for determining the result of an agglutination reaction comprising a reaction step of allowing a sample to react with a reagent in a well, wherein a microplate is used having a plurality of wells arranged in a two-dimensional array, a centrifugation step of centrifuging the microplate according to claim 22, wherein bottom wall of the wells will be arranged outwards with respect to a rotational axis, an imaging step of taking at least one image of the top side of the microplate and at least one image of the bottom side of the microplate, a determination step of determining the sample in said well to be positive or negative with respect to an agglutination reaction, wherein the color intensity and/or the gray level of said well in the images of the top side and the bottom side of the microplate are compared.

27. Method for determining the result of an agglutination reaction comprising a reaction step of allowing a sample to react with a reagent in a well, wherein a microplate is used having a plurality of wells arranged in a two-dimensional array, a centrifugation step of centrifuging the microplate according to claim 23, wherein bottom wall of the wells will be arranged outwards with respect to a rotational axis, an imaging step of taking at least one image of the top side of the microplate and at least one image of the bottom side of the microplate, a determination step of determining the sample in said well to be positive or negative with respect to an agglutination reaction, wherein the color intensity and/or the gray level of said well in the images of the top side and the bottom side of the microplate are compared.

\* \* \* \* \*